US009629677B2

(12) United States Patent
Yasunaga

(10) Patent No.: US 9,629,677 B2
(45) Date of Patent: Apr. 25, 2017

(54) TREATMENT DEVICE FOR MEDICAL TREATMENT

(71) Applicant: OLYMPUS CORPORATION, Tokyo (JP)

(72) Inventor: Shinji Yasunaga, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 371 days.

(21) Appl. No.: 14/172,192

(22) Filed: Feb. 4, 2014

(65) Prior Publication Data

US 2014/0148797 A1 May 29, 2014

Related U.S. Application Data

(63) Continuation of application No. PCT/JP2012/068613, filed on Jul. 23, 2012.

(30) Foreign Application Priority Data

Aug. 5, 2011 (JP) .................................. 2011-172281

(51) Int. Cl.
*A61B 18/08* (2006.01)
*A61B 18/10* (2006.01)
(Continued)

(52) U.S. Cl.
CPC .......... *A61B 18/1445* (2013.01); *A61B 18/10* (2013.01); *A61B 18/085* (2013.01);
(Continued)

(58) Field of Classification Search
CPC ...... A61B 18/10; A61B 18/082; A61B 18/085
See application file for complete search history.

(56) References Cited

U.S. PATENT DOCUMENTS

| 4,219,025 A * | 8/1980 | Johnson | ............... A61B 18/082 219/233 |
| 5,521,850 A * | 5/1996 | Moe | .................... B29C 45/2737 219/505 |

(Continued)

FOREIGN PATENT DOCUMENTS

| JP | 2001-190561 A | 7/2001 |
| JP | 2004-160191 A | 6/2004 |

(Continued)

OTHER PUBLICATIONS

International Search Report dated Aug. 21, 2012 issued in PCT/JP2012/068613.

*Primary Examiner* — Ronald Hupczey, Jr.
(74) *Attorney, Agent, or Firm* — Scully, Scott, Murphy & Presser, P.C.

(57) ABSTRACT

A treatment device for a medical treatment heats a biotissue. The device includes a treatment tool which includes a heat transfer portion and a resistance element, a storage section which stores a time-power list including time-power relations, and a controller. The controller includes a resistance value acquiring section acquiring a resistance value of the resistance element, a power supplying section supplying the power to the resistance element, and a control section. The control section causes the power supplying section to supply a predetermined state detection power in a state detection period, calculates a change of the resistance value in the state detection period, acquires the time-power relation corresponding to the change of the resistance value, and causes the power supplying section to supply the power based on the acquired time-power relation.

20 Claims, 15 Drawing Sheets

(51) Int. Cl.
    *A61B 18/14*     (2006.01)
    *A61B 18/00*     (2006.01)

(52) U.S. Cl.
    CPC ........ *A61B 2018/00589* (2013.01); *A61B 2018/00595* (2013.01); *A61B 2018/00642* (2013.01); *A61B 2018/00702* (2013.01); *A61B 2018/00791* (2013.01); *A61B 2018/087* (2013.01); *A61B 2018/1412* (2013.01); *A61B 2018/1455* (2013.01)

(56) References Cited

U.S. PATENT DOCUMENTS

| | | | | |
|---|---|---|---|---|
| 5,553,622 A * | 9/1996 | McKown | ............... | A61B 5/028 600/505 |
| 5,836,897 A * | 11/1998 | Sakurai | ............ | A61B 17/22012 601/2 |
| 6,997,926 B2 * | 2/2006 | Gellman | ............... | A61B 18/082 606/170 |
| 7,613,523 B2 * | 11/2009 | Eggers | ................ | A61B 18/082 128/898 |
| 8,794,831 B2 * | 8/2014 | Coursey | ................... | G01K 7/20 374/1 |
| 2004/0082971 A1 | 4/2004 | Miura | | |
| 2005/0222560 A1 * | 10/2005 | Kimura | ................ | A61B 18/085 606/28 |
| 2012/0022517 A1 * | 1/2012 | Stuebe | ................ | A61B 18/085 606/31 |
| 2013/0338656 A1 * | 12/2013 | Irisawa | ................ | A61B 18/085 606/27 |

FOREIGN PATENT DOCUMENTS

| | | |
|---|---|---|
| JP | 2005-160733 A | 6/2005 |
| JP | 2005-270141 A | 10/2005 |

\* cited by examiner

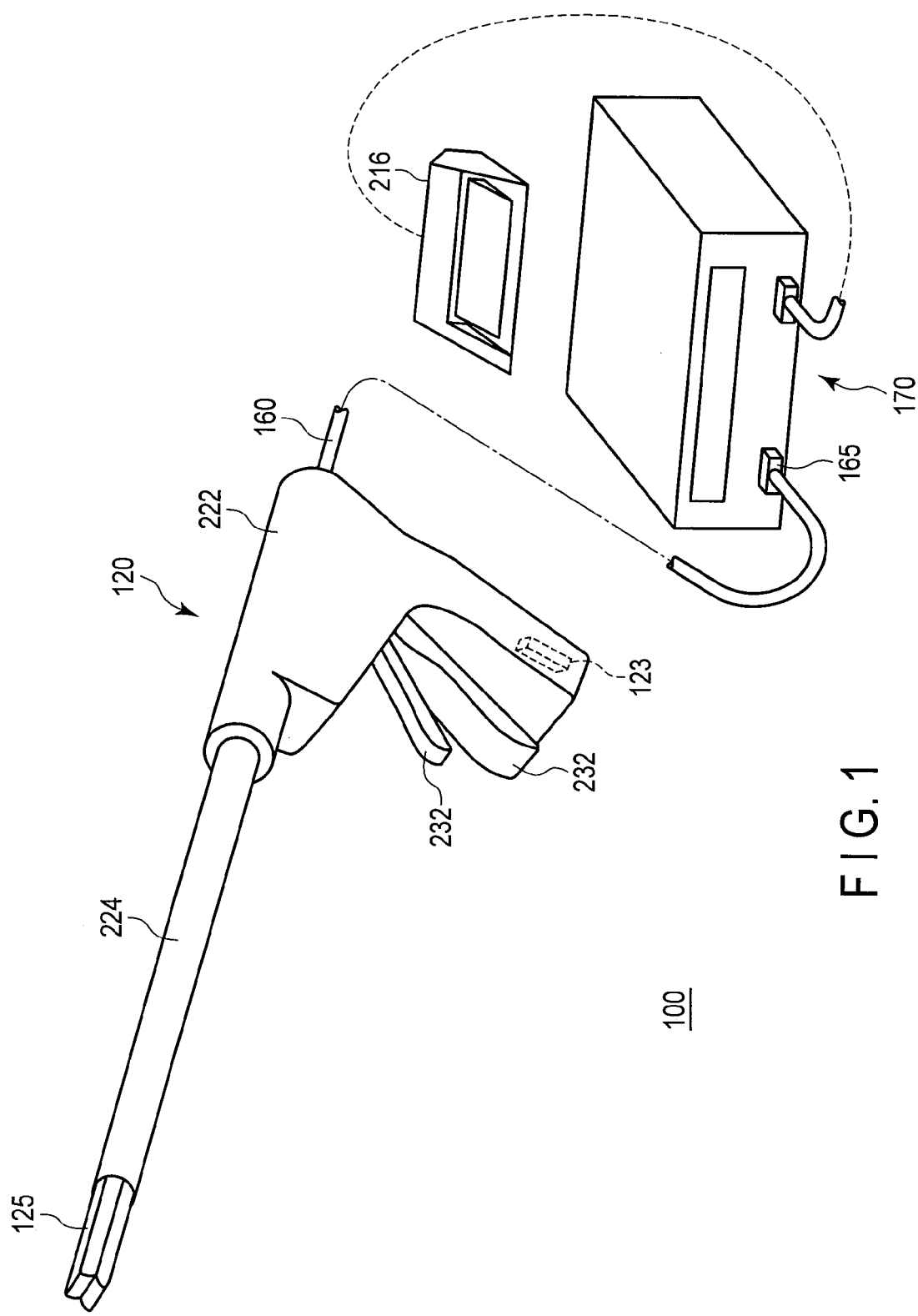
F I G. 1

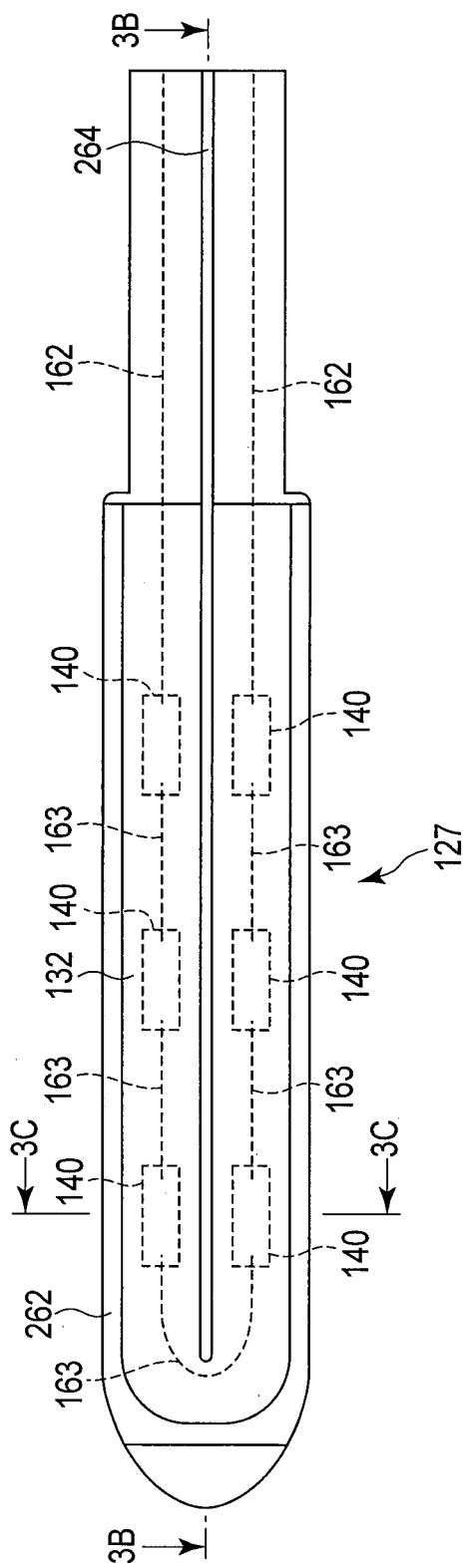
F I G. 3A

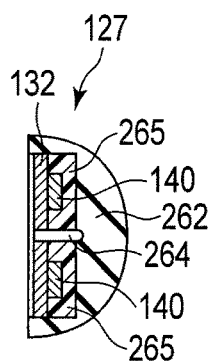
F I G. 3C
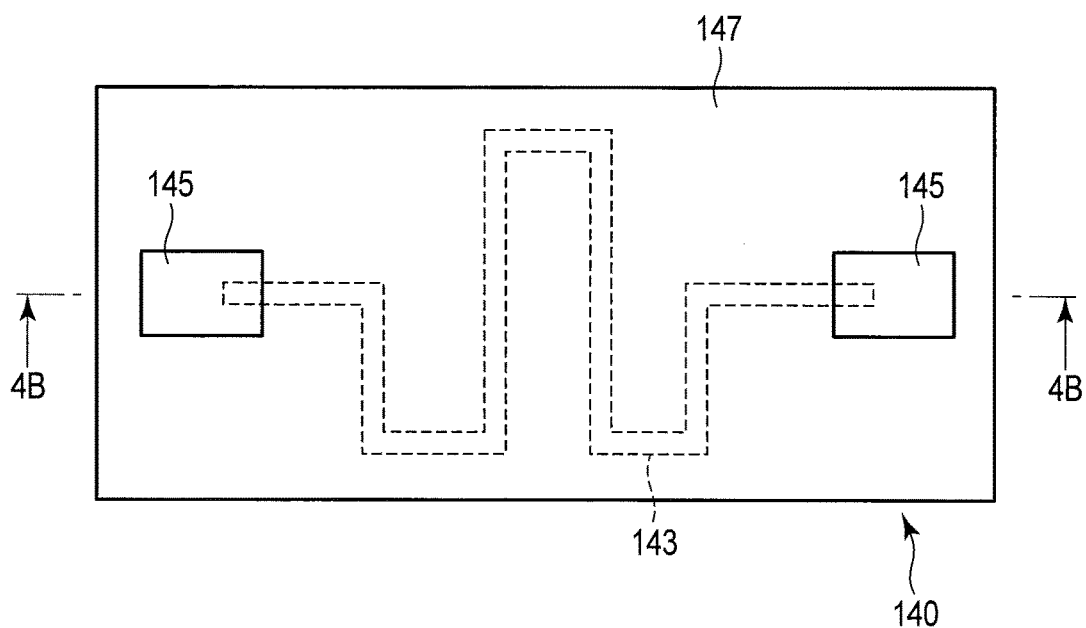
F I G. 4A

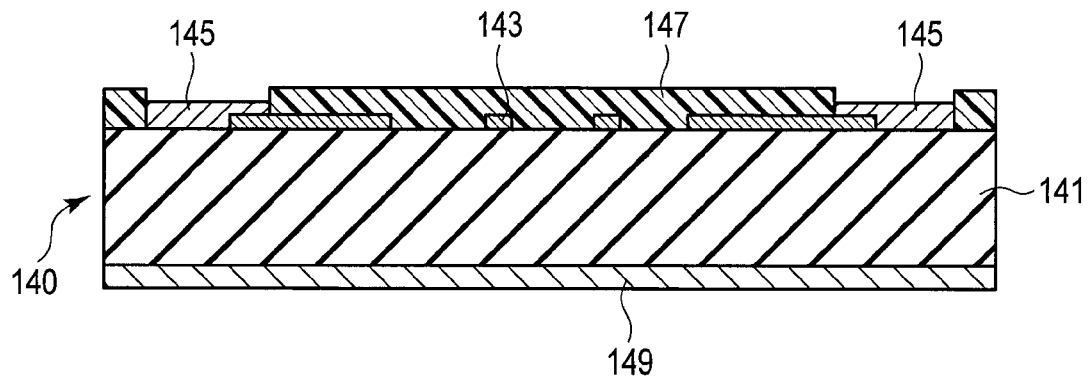
F I G. 4B
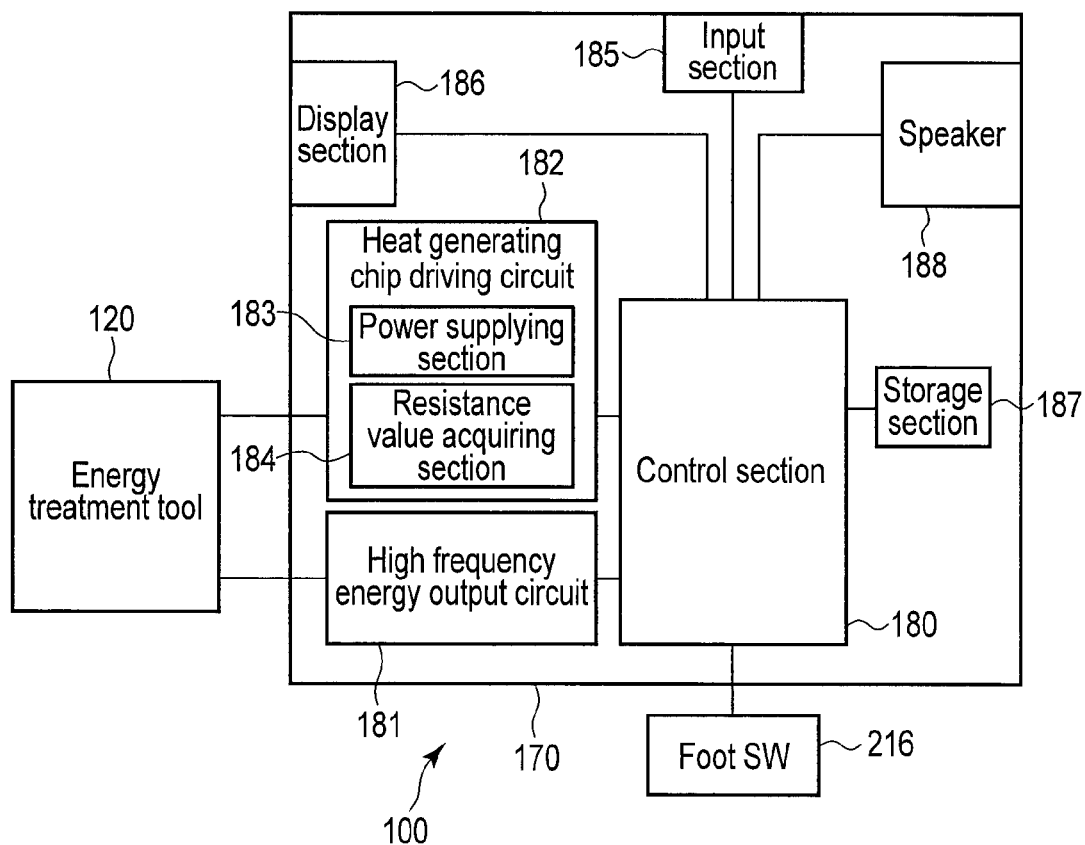
F I G. 5

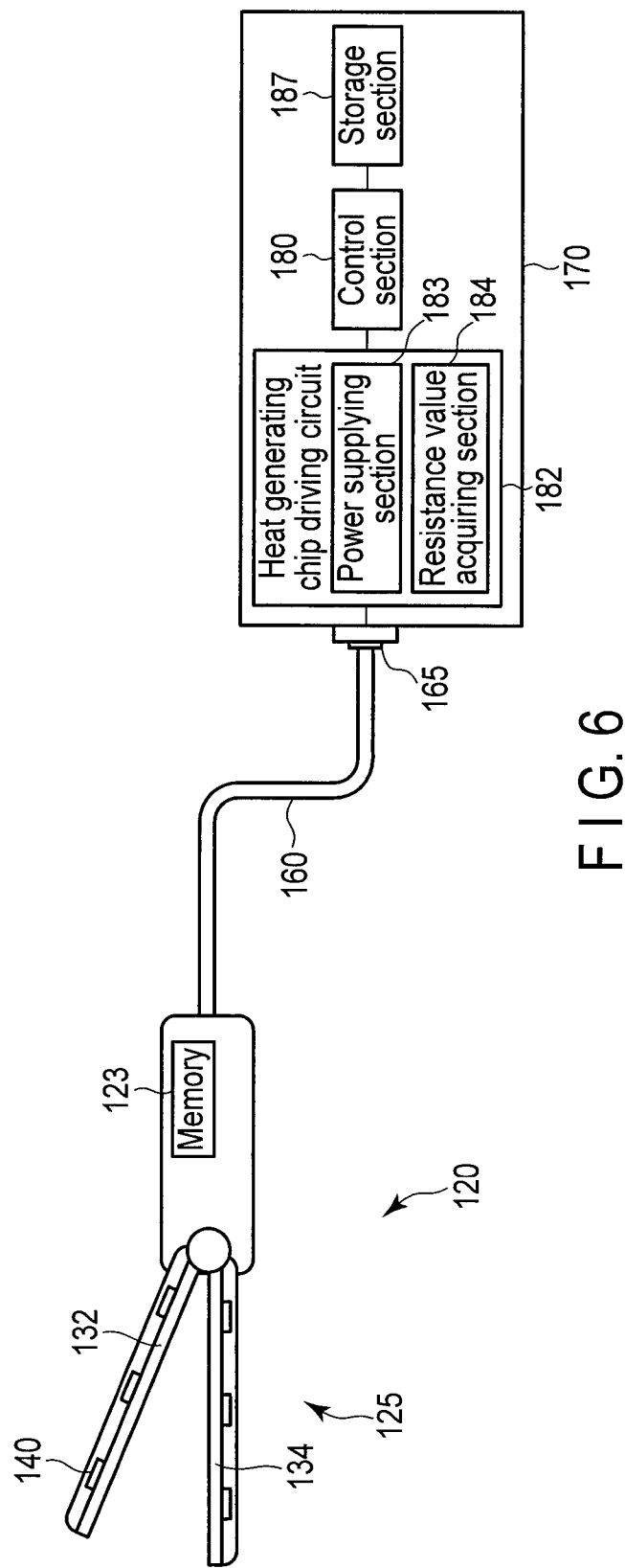
F I G. 6

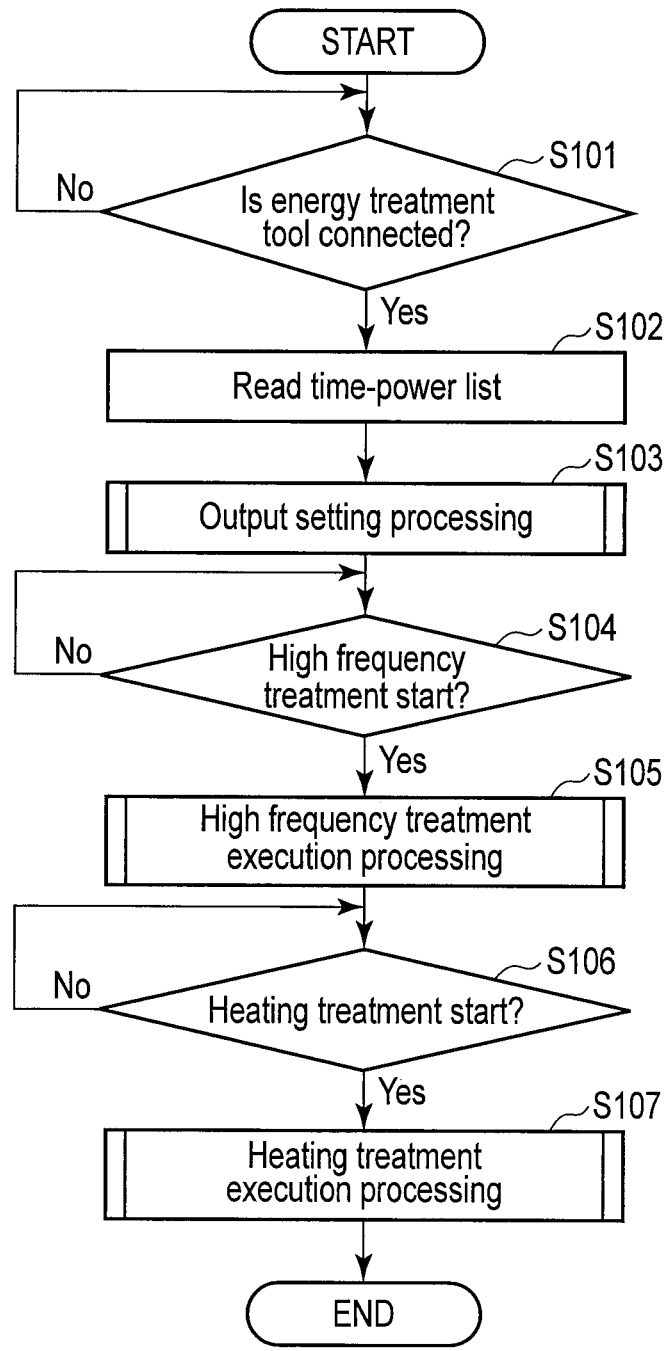
F I G. 7

F I G. 8

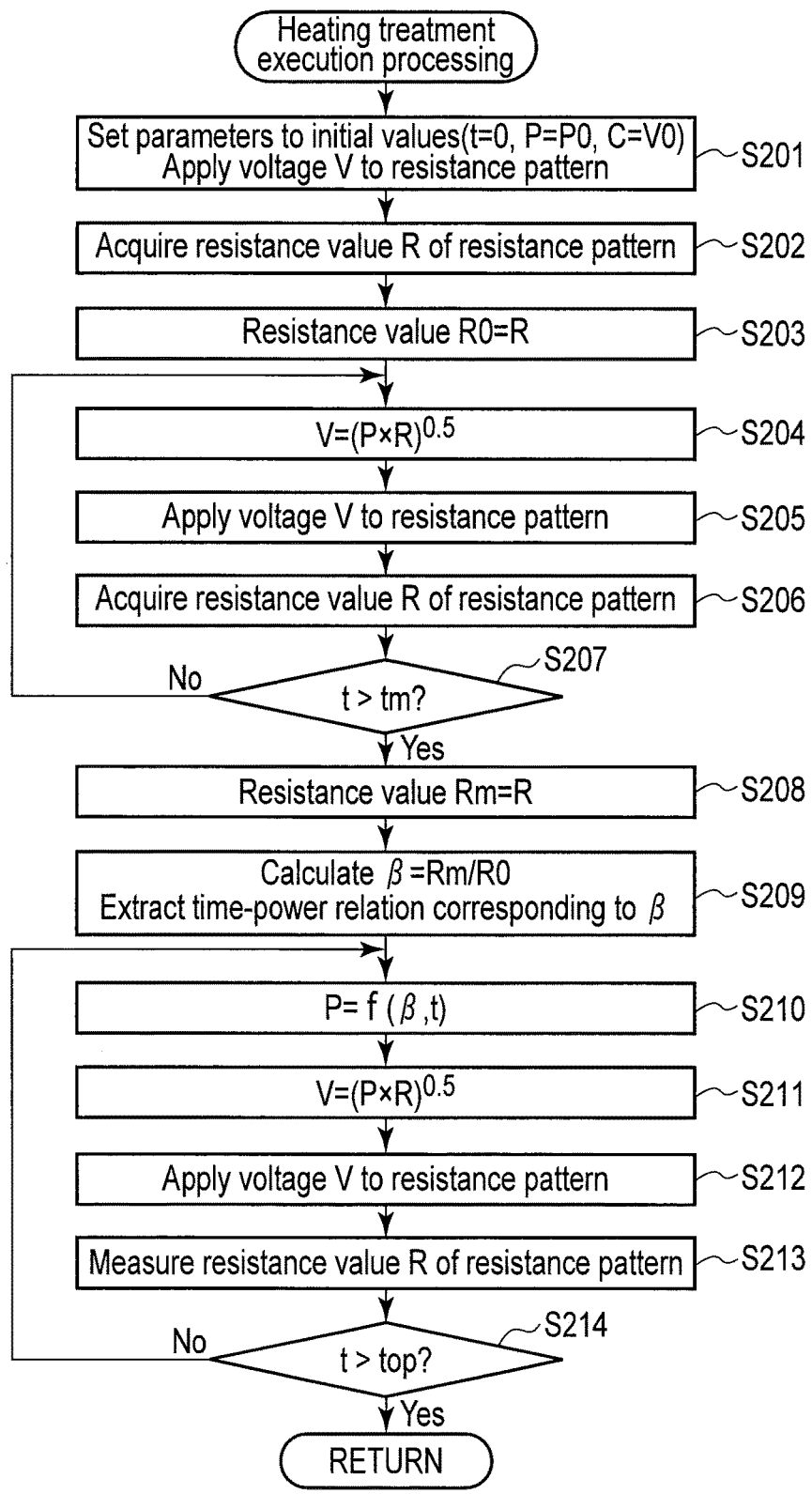
F I G. 9

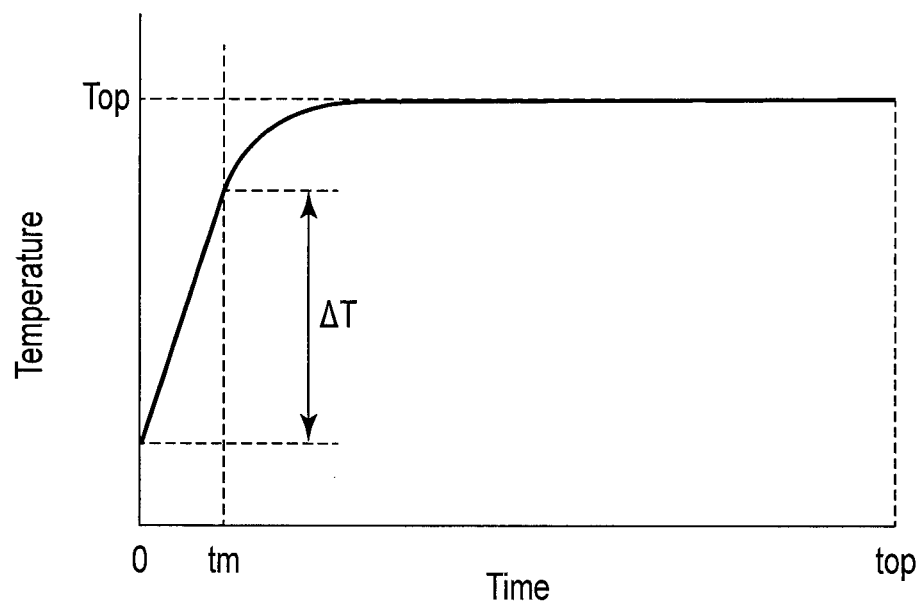
F I G. 10A
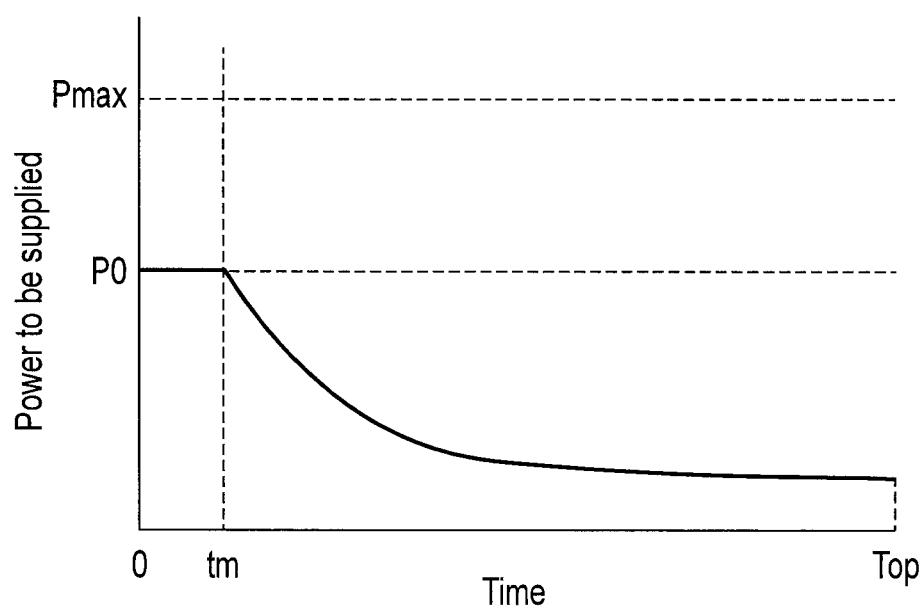
F I G. 10B

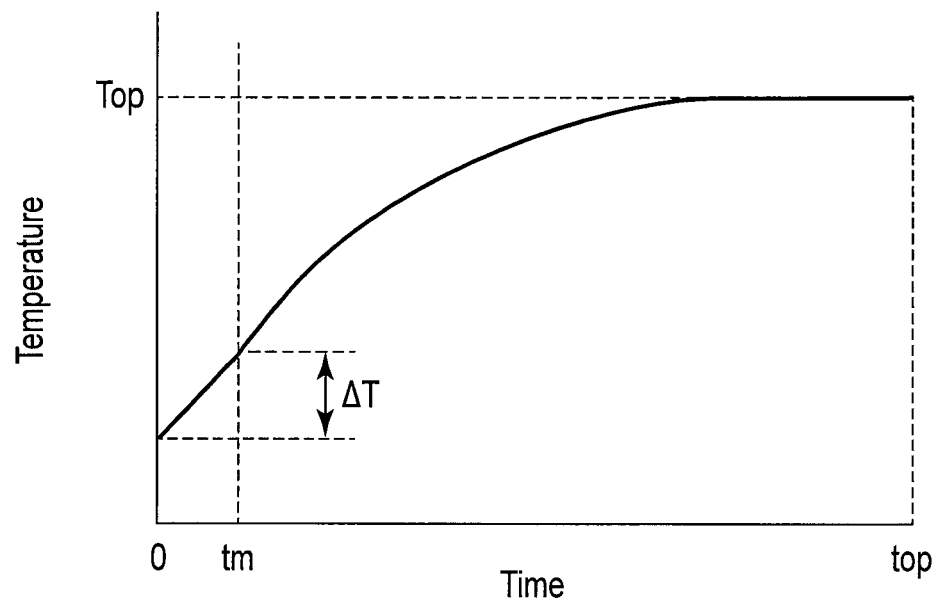
F I G. 12A
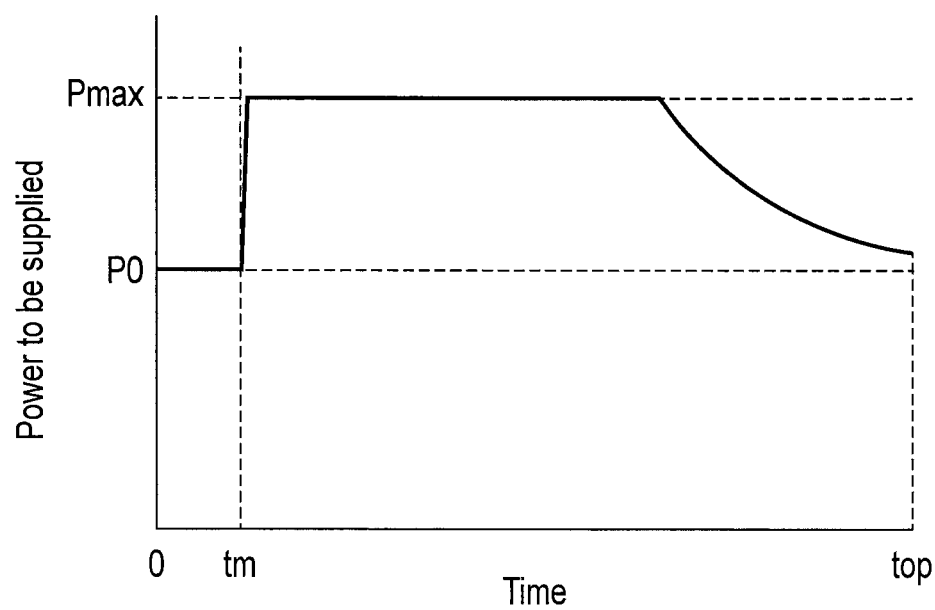
F I G. 12B

| Type A | $\beta$ | | | | | |
|---|---|---|---|---|---|---|
| | | 0.02 | 0.03 | 0.04 | ... | 0.15 | 0.16 |
| Time | tm+0.1 | | | | | | |
| | tm+0.2 | | | | | | |
| | tm+0.3 | | | | | | |
| | ⋮ | | | | | | |
| | ⋮ | | | | | | |
| | top−0.2 | | | | | | |
| | top−0.1 | | | | | | |
| | top | | | | | | |

F I G. 13

TREATMENT DEVICE FOR MEDICAL TREATMENT

CROSS-REFERENCE TO RELATED APPLICATIONS

This application is a Continuation Application of PCT Application No. PCT/JP2012/068613, filed Jul. 23, 2012 and based upon and claiming the benefit of priority from prior Japanese Patent Application No. 2011-172281, filed Aug. 5, 2011, the entire contents of all of which are incorporated herein by reference.

BACKGROUND OF THE INVENTION

1. Field of the Invention

The present invention relates to a treatment device for a medical treatment.

2. Description of the Related Art

In general, a treatment device for a medical treatment is known which treats a biotissue by use of heat energy. For example, in Jpn. Pat. Appln. KOKAI Publication No. 2001-190561, the following treatment device for the medical treatment is disclosed. This treatment device for the medical treatment has an openable/closable holding portion to hold a biotissue that is a treatment object. In this holding portion, a resistance element is disposed which functions as a heater to heat the holding portion. In such a treatment device for the medical treatment, the biotissue is held by the holding portion, and the biotissue of the held portion is heated, whereby the biotissue can be anastomosed. As to control of an amount of power to be supplied to the resistance element, in Jpn. Pat. Appln. KOKAI Publication No. 2001-190561, there are disclosed a control method of supplying the power of the amount of a predetermined constant value, and a method of controlling a temperature of the resistance element to a predetermined temperature by feedback control while performing temperature measurement on the basis of a change of a resistance value of the resistance element.

In use of such a treatment device for a medical treatment as described above, it is general that an area of a biotissue to be held by a holding portion during anastomosis is not constant and varies in every treatment. Consequently, in a control method in which an amount of power to be supplied to a resistance element that functions as a heater is set to a predetermined constant value, an anastomosis temperature varies in every treatment. As a result, there is the possibility that a joining strength becomes unstable. On the other hand, in a method in which the temperature of the resistance element is controlled to a predetermined temperature by feedback control while performing temperature measurement on the basis of a change of a resistance value of the resistance element, it is necessary to accurately acquire characteristics of a relation between the resistance value and the temperature of the resistance element in advance. For this purpose, it is necessary to manage uniformity of the resistance element with high precision during manufacturing, or to accurately measure the resistance-temperature characteristics of the resistance element individually. As a result, costs of the device increase disadvantageously. Furthermore, in the feedback control, the temperature control to be executed tends to be complicated.

BRIEF SUMMARY OF THE INVENTION

An object of the present invention is to provide a treatment device for a medical treatment which can execute temperature control with sufficient precision while simplifying the device and the control to decrease costs.

To achieve the above described object, according to an aspect of the invention, a treatment device for a medical treatment configured to heat a biotissue at a desired temperature to perform the medical treatment includes a treatment tool including a heat transfer portion configured to transfer heat to the biotissue, and a resistance element configured to be supplied power to heat the heat transfer portion; a storage section which stores a time-power list including time-power relations which are relations between an elapsed time and the power to be supplied to the resistance element; and a controller configured to control an operation of the treatment tool, wherein the controller includes a resistance value acquiring section configured to acquire a resistance value of the resistance element; a power supplying section configured to supply the power to the resistance element; and a control section configured to cause the power supplying section to supply a predetermined power as a state detection power, in a state detection period which is a predetermined period, calculate a change of the resistance value in the state detection period based on the resistance value acquired by the resistance value acquiring section, acquire the time-power relation corresponding to the change of the resistance value from the time-power list, and cause the power supplying section to supply the power based on the acquired time-power relation, after elapse of the state detection period.

According to the present invention, there can be provided a treatment device for a medical treatment which can execute the temperature control with sufficient precision while simplifying the device and the control to decrease costs since a power corresponding to a time-power relation acquired on the basis of a resistance value change of a resistance element during supply of a state detection power is supplied to the resistance element.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a configuration example of a treatment device for a medical treatment according to one embodiment of the present invention;

FIG. 3A is a plan view schematically showing a configuration example of a first holding member of the holding portion according to the one embodiment of the present invention;

FIG. 3C is a view schematically showing the configuration example of the first holding member of the holding portion according to the one embodiment of the present invention, and is a cross-sectional view taken along the 3C-3C line of FIG. 3A;

FIG. 4A is a top view schematically showing a configuration example of a heat generating chip according to the one embodiment of the present invention;

FIG. 4B is a view schematically showing the configuration example of the heat generating chip according to the one embodiment of the present invention, and is a sectional view taken along the 4B-4B line shown in FIG. 4A;

FIG. 5 is a view showing a configuration example of a controller according to the one embodiment of the present invention;

FIG. 6 is a view schematically showing one example of a configuration concerning a heating treatment of the treatment device for a medical treatment according to the one embodiment of the present invention;

FIG. 7 is a flowchart showing one example of processing by a control section of the treatment device for the medical treatment according to the one embodiment of the present invention;

FIG. 8 is a diagram schematically showing one example of a time-power list to be stored in a storage section of the treatment device for the medical treatment according to the one embodiment of the present invention;

FIG. 9 is a flowchart showing one example of heating treatment execution processing by the control section of the treatment device for the medical treatment according to the one embodiment of the present invention;

FIG. 10A is a diagram schematically showing a relation between an elapsed time and a temperature of a first high frequency electrode in a case where a contact area between the first high frequency electrode and a biotissue is small;

FIG. 10B is a diagram schematically showing a relation between the elapsed time and a power to be supplied to the heat generating chips in the case where the contact area between the first high frequency electrode and the biotissue is small;

FIG. 12A is a diagram schematically showing a relation between the elapsed time and the temperature of the first high frequency electrode in a case where the contact area between the first high frequency electrode and the biotissue is large;

FIG. 12B is a diagram schematically showing a relation between the elapsed time and the power to be supplied to the heat generating chips in the case where the contact area between the first high frequency electrode and the biotissue is large; and FIG. 13 is a diagram schematically showing one example of a time-power list to be stored in a memory of a treatment device for a medical treatment according to a first modification.

DETAILED DESCRIPTION OF THE INVENTION

Figure 2A:
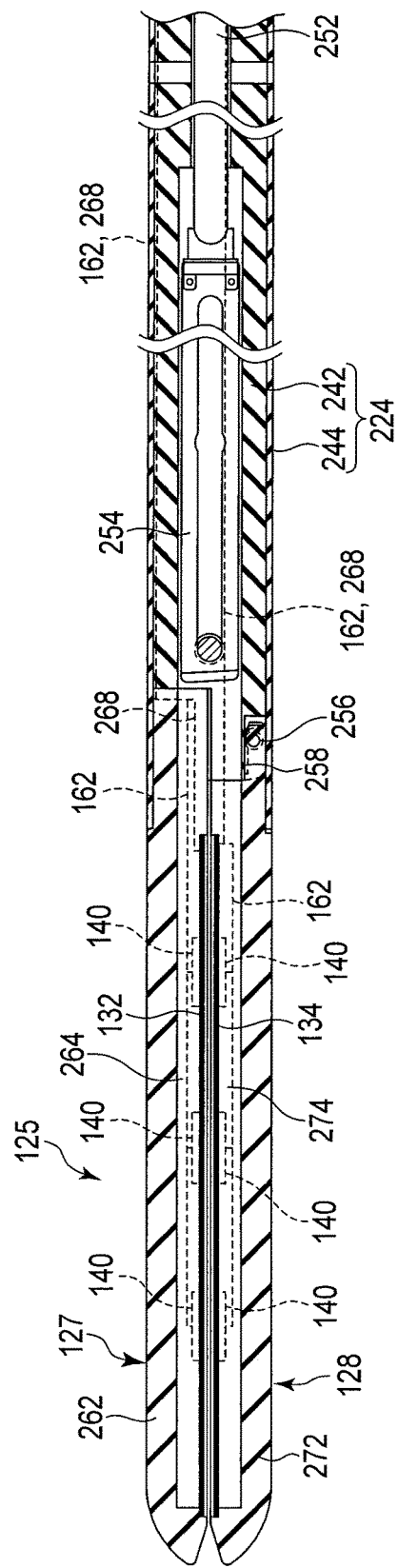
FIG. 2A is a schematic view of a cross section showing a configuration example of a shaft and a holding portion of an energy treatment tool according to the one embodiment of the present invention, and shows a state where the holding portion is closed.

One embodiment of the present invention will be described with reference to the drawings. A treatment device for a medical treatment according to the present embodiment is a device for use in the medical treatment of a biotissue, and a device which applies high frequency energy and heat energy to the biotissue. As shown in FIG. 1, a treatment device 100 for the medical treatment includes an energy treatment tool 120, a controller 170, and a foot switch 216.

The energy treatment tool 120 is a linear type treatment tool for a surgical treatment, for example, for passing through an abdominal wall to perform the treatment. The energy treatment tool 120 has a handle 222, a shaft 224 attached to the handle 222, and a holding portion 125 disposed at the tip of the shaft 224. The holding portion 125 is an openable and closable treatment portion which holds a biotissue of a treatment object, to perform a treatment such as coagulation or incision of the biotissue. Hereinafter, for explanation, a holding portion 125 side will be referred to as a distal side, and a handle 222 side will be referred to as a proximal side. The handle 222 includes operation knobs 232 to operate the holding portion 125. Moreover, a portion of the handle 222 includes a non-volatile memory 123. In the memory 123, as described later in detail, there are stored information such as a type of the energy treatment tool 120 and an identification number inherent in the energy treatment tool 120. It is to be noted that a shape of the energy treatment tool 120 shown herein is, needless to say, one example, and may be any shape as long as the tool has a similar function. For example, the tool may have such a shape as forceps, or the shaft may be bent.

The handle 222 is connected to the controller 170 via a cable 160. Here, the cable 160 is connected to the controller 170 by a connector 165, and this connection is detachable. That is, the treatment device 100 for the medical treatment is configured so that the energy treatment tool 120 can be changed for every treatment. Moreover, to enable the use of a different type of energy treatment tool 120 for every treatment to be performed (e.g., every organ as a subject matter), plural types of energy treatment tools 120 are prepared. In the above-mentioned memory 123, information concerning each of the respective types of energy treatment tools 120 is stored.

The controller 170 is connected to the foot switch 216. The foot switch 216 to be operated by a foot may be replaced with a switch to be operated by a hand or another switch. An operator operates a pedal of the foot switch 216, to switch ON/OFF of supply of energy from the controller 170 to the energy treatment tool 120.

Figure 2B:
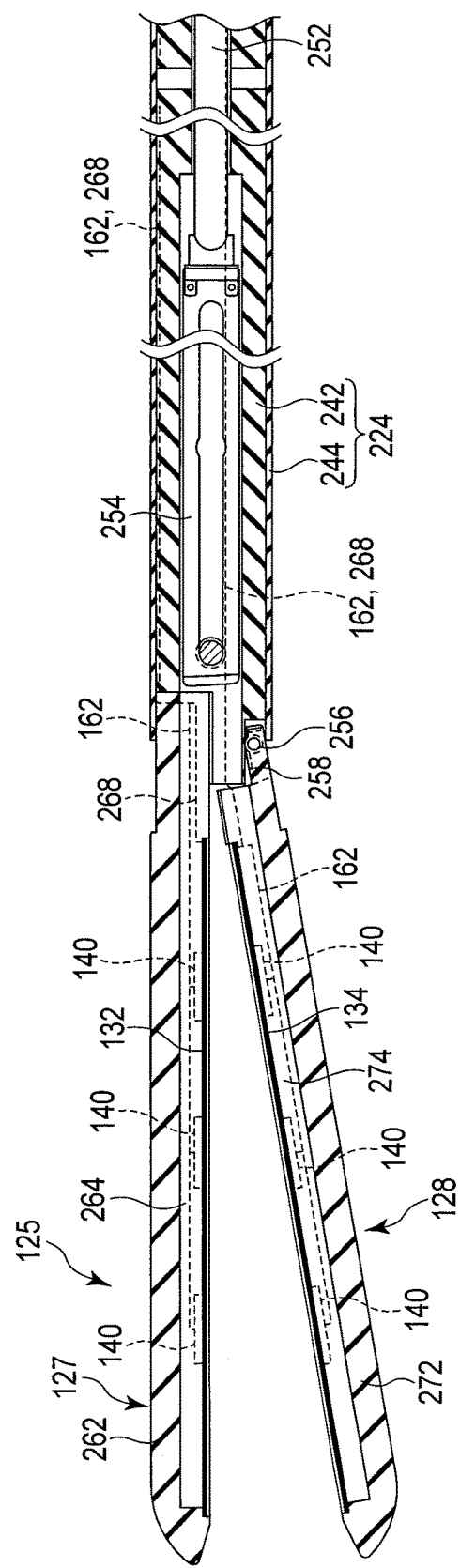
FIG. 2B is a schematic view of a cross section showing the configuration example of the shaft and the holding portion of the energy treatment tool according to the one embodiment of the present invention, and shows a state where the holding portion is opened.

One example of a structure of the holding portion 125 and the shaft 224 is shown in FIGS. 2A and 2B. FIG. 2A shows a state where the holding portion 125 is closed, and FIG. 2B shows a state where the holding portion 125 is opened. The shaft 224 includes a tubular body 242 and a sheath 244. The tubular body 242 is fixed to the handle 222 by a proximal portion of the tubular body. The sheath 244 is disposed on an outer periphery of the tubular body 242 so that the sheath is slidable along an axial direction of the tubular body 242.

In a distal portion of the tubular body 242, the holding portion 125 is disposed. The holding portion 125 includes a first holding member 127 and a second holding member 128. A proximal portion of the first holding member 127 is fixed to the distal portion of the tubular body 242 of the shaft 224. On the other hand, a proximal portion of the second holding member 128 is rotatably supported in the distal portion of the tubular body 242 of the shaft 224 by a support pin 256. Therefore, the second holding member 128 rotates around an axis of the support pin 256, and opens from the first holding member 127 and closes thereto.

In the state where the holding portion 125 is closed, a cross sectional shape of the proximal portion of the first holding member 127 which is combined with the proximal portion of the second holding member 128 is a round shape. The second holding member 128 is urged by an elastic member 258 such as a leaf spring so that the second holding member opens from the first holding member 127. When the sheath 244 is slid along the tubular body 242 to the distal side to cover, with the sheath 244, the proximal portion of the first holding member 127 and the proximal portion of the second holding member 128, the first holding member 127 and the second holding member 128 close against an urging force of the elastic member 258, as shown in FIG. 2A. On the other hand, when the sheath 244 is slid to the proximal side of the tubular body 242, the second holding member 128 opens from the first holding member 127 by the urging force of the elastic member 258, as shown in FIG. 2B.

Into the tubular body 242, as described later, there are inserted energization lines 268 for high frequency electrodes which are to be connected to a first high frequency electrode 132 or a second high frequency electrode 134, and energization lines 162 for heat generating chips which are to be connected to heat generating chips 140 that are heat generation members. In the tubular body 242, a driving rod 252 connected to one of the operation knobs 232 on the proximal side thereof is movably disposed along the axial direction of the tubular body 242. On the distal side of the driving rod 252, a thin plate-like cutter 254 provided with a blade on the distal side is disposed. When the operation knob 232 is operated, the cutter 254 is moved along the axial direction of the tubular body 242 via the driving rod 252. When the cutter 254 moves to the distal side, the cutter 254 is contained in cutter guide grooves 264 and 274 formed in the holding portion 125 as described later.

Figure 3B:
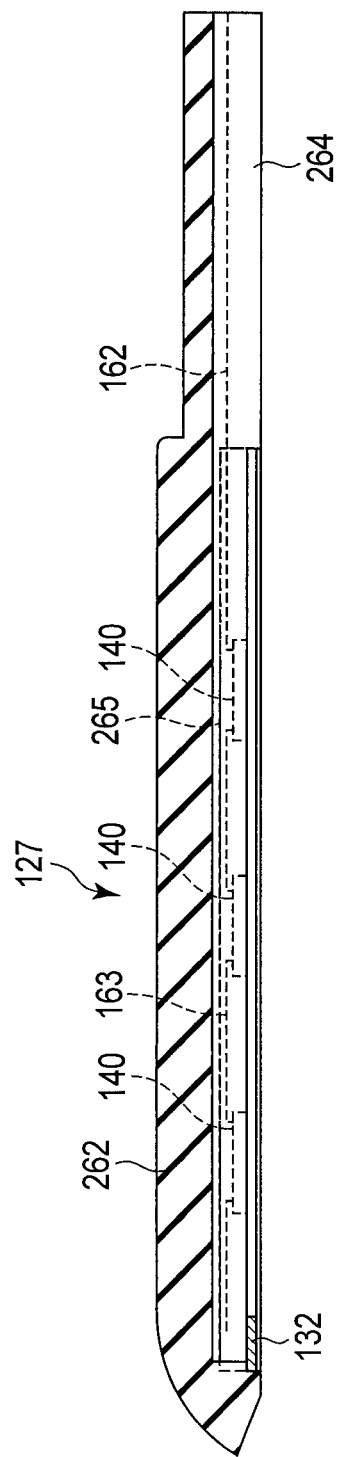
FIG. 3B is a view schematically showing the configuration example of the first holding member of the holding portion according to the one embodiment of the present invention, and is a longitudinal sectional view taken along the 3B-3B line of FIG. 3A.

The first holding member 127 has a first holding member main body 262, and the second holding member 128 has a second holding member main body 272. As shown in FIGS. 3A, 3B and 3C, in the first holding member main body 262, the cutter guide groove 264 is formed to guide the cutter 254 described above. In the first holding member main body 262, a concave portion is disposed, in which the first high frequency electrode 132 made of, for example, a copper thin plate is disposed. The first high frequency electrode 132 has the cutter guide groove 264, and hence a planar shape of the electrode is substantially a U-shape as shown in FIG. 3A.

Furthermore, as described later in detail, the heat generating chips 140 are joined to the surface of the first high frequency electrode 132 on the side of the first holding member main body 262. In such a manner as to cover the heat generating chips 140, wires and the like to the heat generating chips 140 and the first high frequency electrode 132, a sealant made of, for example, silicone is applied to form a sealing film 265. The first high frequency electrode 132 is electrically connected to one of the energization lines 268 for the high frequency electrodes as shown in FIGS. 2A and 2B. The first high frequency electrode 132 is connected to the controller 170 via the energization line 268 for the high frequency electrode which partially passes through the cable 160.

The second holding member 128 has a shape symmetrical to the first holding member 127. That is, at a position of the second holding member 128 which faces the cutter guide groove 264, the cutter guide groove 274 is formed. Moreover, at a position of the second holding member main body 272 which faces the first high frequency electrode 132, the second high frequency electrode 134 is disposed. The second high frequency electrode 134 is connected to the controller 170 via the energization line 268 for the high frequency electrode which partially passes through the cable 160. When the closed holding portion 125 holds the biotissue, the held biotissue comes in contact with the first high frequency electrode 132 and the second high frequency electrode 134.

The first holding member 127 and the second holding member 128 further have mechanisms for heat generation to cauterize the biotissue which comes in contact with the first high frequency electrode 132 and the second high frequency electrode 134. The heat generation mechanism disposed in the first holding member 127 has a configuration similar to that of the heat generation mechanism disposed in the second holding member 128. Here, the heat generation mechanism disposed in the first holding member 127 will be described as an example.

First, the heat generating chips 140 included in this mechanism of the heat generation will be described with reference to FIG. 4A and FIG. 4B. Here, FIG. 4A is a top view, and FIG. 4B is a sectional view taken along the 4B-4B line shown in FIG. 4A. Each of the heat generating chips 140 is formed by using a substrate 141 made of alumina. On a front surface as one of main surfaces of the substrate 141, a resistance pattern 143 as a Pt thin film for the heat generation is formed. Moreover, in the vicinities of two short sides of a rectangular shape of the front surface of the substrate 141, rectangular electrodes 145 are formed, respectively. Here, the electrodes 145 are connected to respective ends of the resistance pattern 143. On the front surface of the substrate 141 excluding portions in which the electrodes 145 are formed and including a portion on the resistance pattern 143, an insulation film 147 made of, for example, a polyimide is formed.

On the whole back surface of the substrate 141, a joining metal layer 149 is formed. The electrodes 145 and the joining metal layer 149 are multilayer films made of, for example, Ti, Cu, Ni, and Au. These electrodes 145 and the joining metal layer 149 are stable during soldering or the like. The joining metal layer 149 is disposed to stabilize the joining, for example, when the heat generating chips 140 are soldered to the first high frequency electrode 132.

The heat generating chips 140 are disposed on the surfaces (second main surfaces) of the first high frequency electrode 132 and the second high frequency electrode 134 on sides opposite to the surfaces (first main surfaces) thereof which come in contact with the biotissue. Here, the heat generating chips 140 are fixed, respectively, by soldering the front surface of the joining metal layer 149 to the second main surface of the first high frequency electrode 132 or the second high frequency electrode 134.

The case of the first high frequency electrode 132 will be described as an example with reference to FIGS. 3A, 3B and 3C. In the first high frequency electrode 132, the six heat generating chips 140 are disposed in a discrete manner. That is, the heat generating chips 140 are arranged every three chips in each of two rows symmetrically via the cutter guide groove 264 from the proximal side toward the distal side.

The resistance patterns 143 of these heat generating chips 140 are connected in series via the electrodes 145. The adjacent electrodes 145 are connected to each other by a wire 163 formed, for example, by wire bonding. Both ends of the heat generating chips connected in series are connected to a pair of energization lines 162 for the heat generating chips. The pair of energization lines 162 for the heat generating chips partially pass through the cable 160, and are connected to the controller 170. In this way, the heat generating chips 140 are connected to the controller 170 via the wire 163 and the energization lines 162 for the heat generating chips. The controller 170 controls a power to be supplied to the heat generating chips 140.

As above, in the present embodiment, the heat generating chips 140 are disposed in the first high frequency electrode 132, but this disposition is for the purpose of enhancing temperature uniformity of the first high frequency electrode 132, and it can also be regarded that all six heat generating chips 140 electrically constitute a single heat generating chip. A current output from the controller 170 flows through the respective resistance patterns 143 of the six heat generating chips 140. As a result, the respective resistance patterns 143 generate heat. When the resistance patterns 143 generate the heat, the heat is transferred to the first high frequency electrode 132. By this heat, the biotissue which comes in contact with the first high frequency electrode 132 is cauterized.

For efficiently transferring the heat generated in the heat generating chips 140 to the first high frequency electrode 132, each of the sealing film 265 and the first holding member main body 262 around the film preferably has a thermal conductivity lower than a thermal conductivity of the first high frequency electrode 132 or the substrate 141. The low thermal conductivity of each of the sealing film 265 and the first holding member main body 262 thus makes it possible to realize heat conduction with less loss.

In the controller 170, as shown in FIG. 5, there are disposed a control section 180, a high frequency energy output circuit 181, a heat generating chip driving circuit 182, an input section 185, a display section 186, a storage section 187, and a speaker 188. The control section 180 is connected to each section in the controller 170, to control each section of the controller 170. The high frequency energy output circuit 181 is connected to the energy treatment tool 120, and drives the first high frequency electrode 132 and the second high frequency electrode 134 of the energy treatment tool 120 under the control of the control section 180. That is, the high frequency energy output circuit 181 applies a high frequency voltage to the first high frequency electrode 132 and the second high frequency electrode 134 via the energization lines 268 for the high frequency electrodes.

The heat generating chip driving circuit 182 is connected to the energy treatment tool 120, and drives the heat generating chips 140 of the energy treatment tool 120 under the control of the control section 180. The heat generating chip driving circuit 182 has a power supplying section 183 and a resistance value acquiring section 184. The power supplying section 183 supplies a power to the resistance patterns 143 of the heat generating chips 140 for the purpose of heating via the energization lines 162 for the heat generating chips under the control of the control section 180. Here, the power supplying section 183 can change an amount of the power to be supplied to the heat generating chips 140.

A current output from the power supplying section 183 flows through the respective resistance patterns 143 of the heat generating chips 140 via the energization lines 162 for the heat generating chips, so that heat is generated in the resistance patterns 143. By the heat generated in the resistance patterns 143, a temperature of the first high frequency electrode 132 and the second high frequency electrode 134 rises. As a result, the biotissue which comes in contact with the first high frequency electrode 132 or the second high frequency electrode 134 is cauterized and coagulated. The control section 180 controls the power supplying section 183 so that the temperature of the first high frequency electrode 132 and the second high frequency electrode 134 reaches a desired temperature.

The resistance value acquiring section 184 of the heat generating chip driving circuit 182 has a function of measuring the current which flows when the voltage is applied to the heat generating chips 140. The resistance value acquiring section 184 calculates a resistance value of the resistance patterns 143 on the basis of a value of the voltage applied to the resistance patterns 143 and a value of the current which flows at this time. The resistance value acquiring section 184 outputs the calculated resistance value to the control section 180.

The resistance value of the resistance patterns 143 changes in accordance with a temperature of the resistance patterns 143. The control section 180 calculates a value concerning a temperature change of the resistance patterns 143 on the basis of the resistance value change of the resistance patterns 143. This temperature change of the resistance patterns 143 takes place in accordance with a contact state between the first high frequency electrode 132 or the second high frequency electrode 134 in which the heat generating chips 140 are disposed and the biotissue. For example, the larger a contact area between the first high frequency electrode 132 or the second high frequency electrode 134 and the biotissue is, the smaller the temperature change during the supply of the same power becomes.

The control section 180 controls the heat generating chips 140 as described later in detail. In brief, the control section 180 supplies a predetermined power P0 as a state detection power to the heat generating chips 140 in a period as a state detection period from start of the heating to predetermined time tm. The control section 180 acquires, from the resistance value acquiring section 184, the resistance value of the resistance patterns 143 of the heat generating chips during the supply of this predetermined power P0, and calculates the change thereof. The control section 180 then determines an amount of the power to be supplied to the heat generating chips 140 until a treatment time top elapses, in accordance with the change of the calculated resistance value. Here, the amount of the power to be supplied until the treatment time top elapses from the time tm is predetermined as a time-power relation. The storage section 187 stores a time-power list including these time-power relations. The control section 180 selects one time-power relation from the time-power relations stored in the storage section on the basis of the change of the resistance value of the resistance patterns 143 during the supply of the predetermined power P0, and controls the power supplying section 183 on the basis of the relation. It is to be noted that the treatment time top is, for example, about 30 seconds.

The control section 180 is connected to the foot switch (SW) 216, and ON indicating that a treatment by the energy treatment tool 120 is to be performed and OFF indicating that the treatment is to be stopped are input from the foot switch 216. The input section 185 is input various settings and the like of the control section 180. The display section 186 displays various pieces of information of the treatment device 100 for the medical treatment under the control of the control section 180. In the storage section 187, various pieces of data required for an operation of the controller 170 are stored in addition to the above-mentioned time-power list. The speaker 188 outputs an alarm sound or the like.

A schematic view in which a portion concerning a heating treatment is especially extracted from the treatment device 100 for the medical treatment described above is shown in FIG. 6. As shown in this drawing, the heating treatment is performed by the energy treatment tool 120 including the holding portion 125 having the first high frequency electrode 132 and the second high frequency electrode 134 and the heat generating chips 140, and the memory 123. The control of the energy treatment tool 120 is executed by the controller 170 including the control section 180, the heat generating chip driving circuit 182 having the power supplying section 183 and the resistance value acquiring section 184, and the storage section 187. The energy treatment tool 120 is connected to the controller 170 via the detachable cable 160 by use of the connector 165 disposed on the side of the controller 170. It is to be noted that the above-mentioned configuration concerning the high frequency treatment or the cutter is not necessarily required in the treatment device 100 for the medical treatment.

In this way, for example, the first high frequency electrode 132 or the second high frequency electrode 134 functions as a heat transfer portion which transfers the heat to the biotissue. For example, the heat generating chips 140 function as resistance elements into which the power is supplied to heat the heat transfer portions. For example, the energy treatment tool 120 functions as a treatment tool having the heat transfer portions and the resistance elements. For example, the storage section 187 functions as a storage section to store the time-power list including the time-power relations as the relations between the elapsed time and the power to be supplied to the resistance elements. For example, the controller 170 functions as a controller which controls the operation of the treatment tool. For example, the power supplying section 183 functions as a power supplying section which supplies the power to the resistance elements. For example, the resistance value acquiring section 184 functions as a resistance value acquiring section which acquires the resistance value of the resistance elements. For example, the control section 180 functions as a control section which causes the power supplying section to supply the state detection power in the state detection period, calculates the change of the resistance value in the state detection period, acquires the time-power relation corresponding to the change of the resistance value, and causes the power supplying section to supply the power on the basis of the time-power relation after the elapse of the state detection period.

Next, an operation of the treatment device 100 for the medical treatment according to the present embodiment will be described. A flowchart showing a processing executed by the control section 180 is shown in FIG. 7. In step S101, the control section 180 determines whether or not the cable 160 connected to the energy treatment tool 120 is connected to the controller 170 via the connector 165. When the cable is not connected, the control section 180 repeats the step S101. On the other hand, when the control section 180 determines that the cable 160 connected to the energy treatment tool 120 is connected to the controller 170, the processing goes to step S102.

Figure 8:
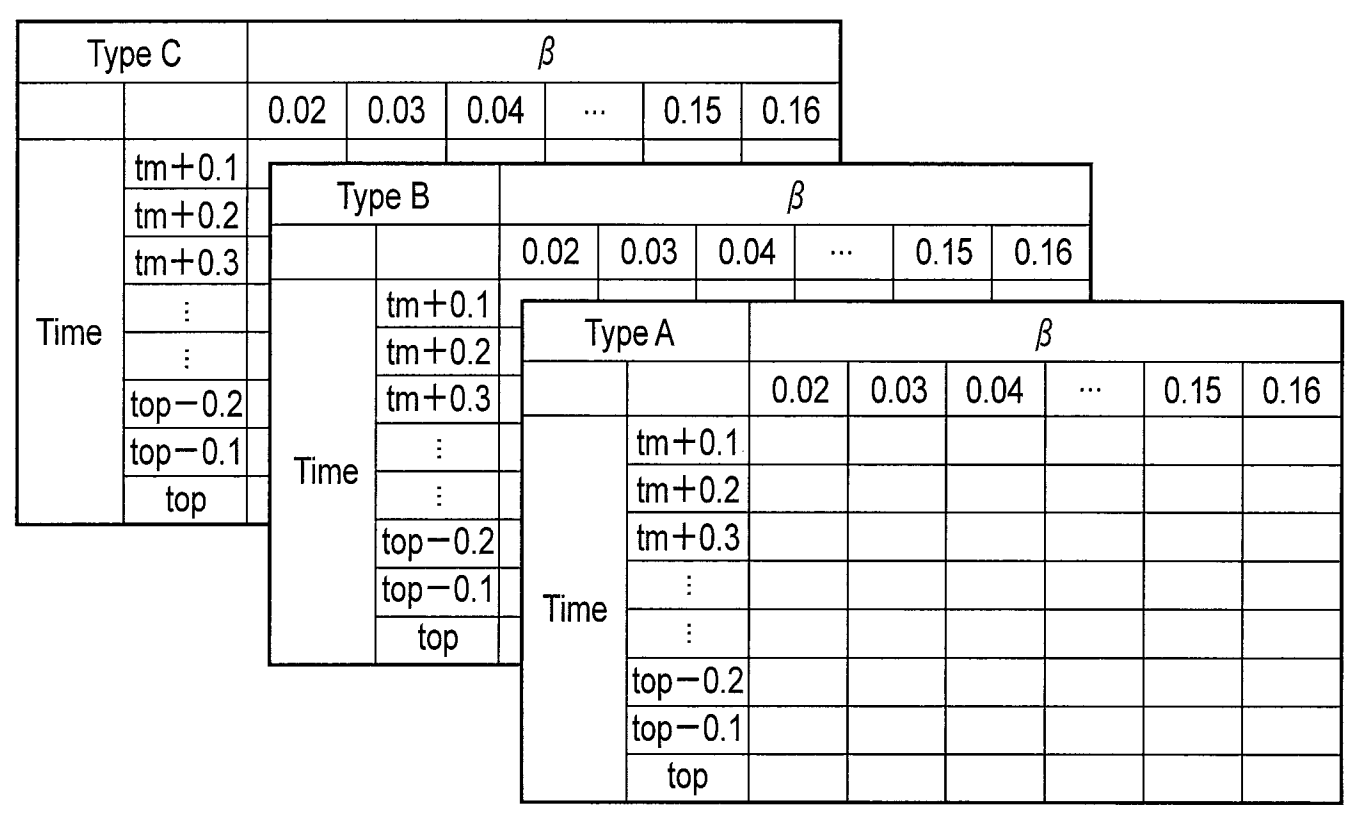

In step S102, the control section 180 reads the time-power list stored in the storage section 187 in accordance with the type of connected energy treatment tool 120. The time-power list is, for example, a table shown in FIG. 8. In the time-power list, for example, values of a power P at times tm to top, i.e., the time-power relations are recorded for each variable β. Such a time-power list is prepared for each type of energy treatment tool 120. The time-power list is stored, for example, in the storage section 187. For example, when the energy treatment tool 120 connected to the controller 170 is a type A, the control section 180 reads the time-power list corresponding to the type A from the storage section 187, and when the energy treatment tool 120 is a type B, the control section 180 reads the time-power list corresponding to the type B from the storage section 187. The type of energy treatment tool 120 is stored, for example, in the memory 123 of the energy treatment tool 120. When the energy treatment tool 120 is connected to the controller 170, the control section 180 reads information stored in the memory 123 to determine the type of energy treatment tool 120. It is to be noted that the time-power list is not limited to a table shown in FIG. 8. For example, a polynomial equation indicating the relation between the time and the power may be given.

In step S103, the control section 180 executes an output setting processing which is a defined processing. In the output setting processing, the control section 180 receives an operator's instruction via the input section 185, and sets output conditions of the treatment device 100 for the medical treatment, for example, a set power of a high frequency energy output, and the like. Here, the operator may individually set each value, or the operator may select a set of the set values in accordance with an operation type and the control section 180 may determine the output conditions on the basis of the selection.

The holding portion 125 and the shaft 224 of the energy treatment tool 120 are inserted, for example, into an abdominal cavity through the abdominal wall. The operator operates the operation knobs 232 to open and close the holding portion 125, so that the biotissue of the objective matter for treatment is held by the first holding member 127 and the second holding member 128. At this time, the biotissue of the objective matter for treatment comes in contact with the first main surfaces of both the first high frequency electrode 132 disposed in the first holding member 127 and the second high frequency electrode 134 disposed in the second holding member 128.

In step S104, the control section 180 repeats determination of whether or not the instruction of high frequency treatment start by the operator has been input. The operator operates the foot switch 216, when the biotissue of the objective matter for treatment is held by the holding portion 125. For example, the foot switch 216 is switched ON, and the control section 180 determines that the instruction of the high frequency treatment start is input. At this time, in step S105, the control section 180 executes a high frequency treatment execution processing. In the high frequency treatment execution processing, a high frequency power of the set power is supplied from the high frequency energy output circuit 181 of the controller 170 to the first high frequency electrode 132 and the second high frequency electrode 134 via the cable 160. The power to be supplied is, for example, from about 20 W to 80 W. As a result, the biotissue generates the heat, and the biotissue is cauterized. By this cauterization, the biotissue is denatured and coagulated. After elapse of a predetermined time or on the basis of the operator's instruction, the control section 180 stops the output of the high frequency energy, and the high frequency treatment execution processing ends.

In step S106, the control section 180 repeats determination of whether or not the instruction of heating treatment start has been input by the operator. For example, when the foot switch 216 is switched ON and the control section 180 determines that the instruction of the heating treatment start is input, the control section 180 executes a heating treatment execution processing in step S107. In the heating treatment execution processing, the controller 170 supplies the power to the heat generating chips 140 so that the temperature of the first high frequency electrode 132 and the second high frequency electrode 134 reaches the desired temperature, as described later in detail. Here, the desired temperature is, for example, about 200° C. At this time, the current flows through the resistance patterns 143 of the respective heat generating chips 140 from the power supplying section 183 of the heat generating chip driving circuit 182 of the controller 170 via the energization lines 162 for the heat generating chips. The resistance patterns 143 of the respective heat generating chips 140 generate the heat by the current.

The heat generated in the resistance patterns 143 is transferred to the first high frequency electrode 132 and the second high frequency electrode 134 via the substrate 141 and the joining metal layer 149. As a result, the temperature of the first high frequency electrode 132 and the second high frequency electrode 134 rises. By this heat, the biotissue which comes in contact with the first main surface of the first high frequency electrode 132 or the second high frequency electrode 134 is further cauterized and further coagulated. When a predetermined treatment time elapses, the output of the heat energy is stopped, and the heating treatment execution processing ends. As described above, a series of processes by the control section 180 ends. Finally, the operator operates the operation knobs 232 to move the cutter 254, and cuts the biotissue. As above, the treatment of the biotissue is completed.

Next, the heating treatment execution processing will be described. An outline of the heating treatment execution processing is as follows. The control section 180 causes the power supplying section 183 of the heat generating chip driving circuit 182 to supply the predetermined power P0 as the state detection power into the heat generating chips 140 for the time tm. Here, the time tm is, for example, about 0.5 or 1 second.

The resistance value of the resistance patterns 143 at the start of the supply of the power P0 is a resistance value R0, and the resistance value of the resistance patterns 143 at the time tm is a resistance value Rm. At this time, a temperature rise ΔT of the first high frequency electrode 132 or the second high frequency electrode 134 at the time tm can be represented by Equation (1) in the following:

$$\Delta T = (Rm/R0 - 1)/\alpha, \quad (1)$$

where α is a temperature coefficient of resistance (TCR) of the resistance patterns 143. TCR is a constant determined by a material which forms the resistance patterns 143. That is, this constant does not depend on a linear width or a thickness of the resistance patterns 143 in which non-uniformity occurs in a manufacturing process. Therefore, in the heat generating chips 140 using the same material and having the same structure, a difference in α is remarkably small, and the difference in α is also remarkably small between the energy treatment tools 120 of the same type. From the above, the control section 180 supplies the predetermined power P0 until the time tm to acquire the resistance value R0 and the resistance value Rm, whereby the temperature rise ΔT can be calculated.

In the present embodiment, the control section 180 determines the subsequent power to be supplied to the heat generating chips 140 on the basis of a value concerning the temperature rise ΔT calculated in this manner, i.e., the variable β=Rm/R0. For example, when the temperature rise ΔT (the variable β) is comparatively large, an area of the first high frequency electrode 132 or the second high frequency electrode 134 which comes in contact with the biotissue is comparatively small. In this case, the control section 180 comparatively decreases the power to be subsequently supplied. On the other hand, when the temperature rise ΔT (the variable β) is comparatively small, the area of the first high frequency electrode 132 or the second high frequency electrode 134 which comes in contact with the biotissue is comparatively large. In this case, the control section 180 comparatively increases the power to be subsequently supplied.

The heating treatment execution processing will be described with reference to a flowchart shown in FIG. 9. In step S201, the control section sets various parameters to initial values. For example, the control section 180 resets time t to 0 to start measurement of the time. Moreover, the control section 180 sets the power to be supplied to the heat generating chips 140 to the predetermined power P0. Further, the control section 180 sets a voltage V to be applied to the resistance patterns 143 of the heat generating chips 140 to an initial value V0, and causes the power supplying section 183 to apply the voltage to the resistance patterns.

In step S202, the control section 180 causes the resistance value acquiring section 184 of the heat generating chip driving circuit 182 to acquire the resistance value R of the resistance patterns 143 which is calculated on the basis of a current I0 flowing when the voltage V0 is applied. In step S203, the control section 180 stores the resistance value R acquired in step S202 as the resistance value R0 at the start of the power supply.

In step S204, the control section 180 calculates the voltage V to be applied to the resistance patterns 143 in accordance with $V=(P \times R)^{0.5}$ on the basis of the power P to be supplied=P0 set in step S201 and the resistance value R. In step S205, the control section 180 causes the power supplying section 183 of the heat generating chip driving circuit 182, to apply the voltage V calculated in step S204 to the resistance patterns 143. In step S206, the control section 180 acquires the resistance value R of the resistance patterns 143 in the same manner as in step S202. In step S207, the control section 180 determines whether or not the time t is larger than the predetermined time tm. When the time t is the time tm or less, the processing returns to the step S204. That is, the predetermined power P0 is supplied to the heat generating chips 140 until the predetermined time tm.

In the determination of the step S207, when the time t is larger than the time tm, the processing goes to step S208. In step S208, the control section 180 stores the resistance value Rm of the resistance patterns 143 at the time tm. In step S209, the control section 180 calculates the variable β in accordance with β=Rm/R0. This variable β is a value concerning the temperature rise ΔT. Furthermore, the control section 180 extracts a time-power relation P=f(β, t) corresponding the calculated variable β from the time-power list read in step S102.

In step S210, the control section 180 determines the power P to be supplied to the heat generating chips 140 at the time t in accordance with the time-power relation P=f(β, t). In step S211, the control section 180 calculates the voltage V to be applied to the resistance patterns 143 of the heat generating chips 140 which is required to supply the power P in accordance with $V=(P \times R)^{0.5}$. In step S212, the control section 180 controls the power supplying section 183 to apply the voltage V calculated in step S211 to the resistance patterns 143. In step S213, the control section 180 acquires the resistance value R of the resistance patterns 143 in the same manner as in step S202. In step S214, the control section 180 determines whether or not the time t is larger than the treatment time top. When the time t is the treatment time top or less, the processing returns to the step S210. That is, the power P corresponding to the time-power relation is supplied to the heat generating chips 140 until the treatment time top elapses. Here, the treatment time top is, for example, about 30 seconds. In the determination of the step S214, when the time t is larger than the treatment time top, the processing returns to the step S207. In this way, for example, the time 0 to tm corresponds to the state detection period.

As to a relation between the temperature of the first high frequency electrode 132 and the power to be supplied with elapse of time, three examples where a contact state of the first high frequency electrode 132 with the biotissue varies are shown in FIG. 10A, FIG. 10B, FIG. 11A, FIG. 11B, FIG. 12A and FIG. 12B. As shown in FIG. 10A, it is considered that when the temperature rise $\Delta T=(Rm/R0-1)/\alpha$ is comparatively large, i.e., when the variable $\beta$ is comparatively large, the contact area between the first high frequency electrode 132 and the biotissue is comparatively small. The time-power relation $P=f(\beta, t)$ for use in this case is, for example, a relation shown in FIG. 10B. That is, after the time tm, the power P to be supplied has such a relation as to decrease gradually, and after the elapse of the predetermined time, a constant power is supplied. By this supply of the power, the temperature of the first high frequency electrode 132 is maintained at a desired temperature Top as shown in FIG. 10A.

Figure 11A:
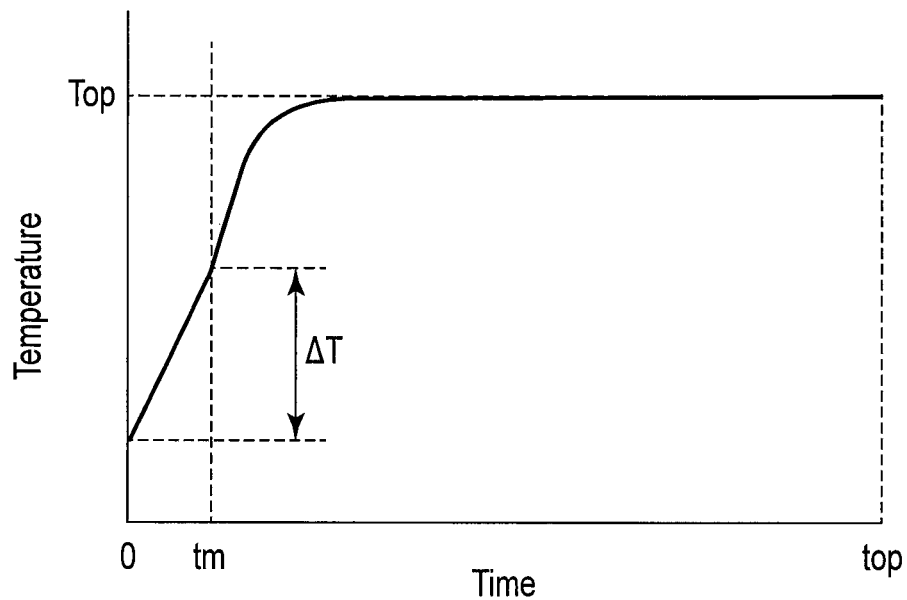
FIG. 11A is a diagram schematically showing a relation between the elapsed time and a temperature of the first high frequency electrode in a case where the contact area between the first high frequency electrode and the biotissue is moderate.

As shown in FIG. 11A, it is considered that when the temperature rise $\Delta T$ is moderate, i.e., when the variable $\beta$ is moderate, the contact area between the first high frequency electrode 132 and the biotissue is moderate. The time-power relation $P=f(\beta, t)$ for use in this case is, for example, a relation shown in FIG. 11B. That is, after the time tm, the power P to be supplied rises to a maximum power Pmax to be supplied, this power is maintained for a short time, and then the power gradually decreases down to the constant power. By this supply of the power, the temperature of the first high frequency electrode 132 is maintained at the desired temperature Top as shown in FIG. 11A.

Figure 11B:
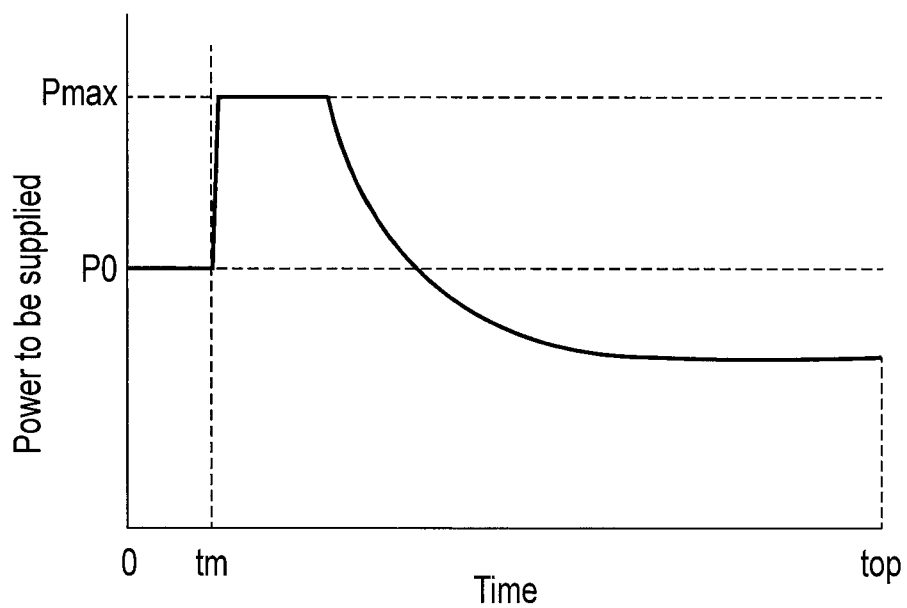
FIG. 11B is a diagram schematically showing a relation between the elapsed time and the power to be supplied to the heat generating chips in the case where the contact area between the first high frequency electrode and the biotissue is moderate.

As shown in FIG. 12A, it is considered that when the temperature rise $\Delta T$ is comparatively small, i.e., when the variable $\beta$ is comparatively small, the contact area between the first high frequency electrode 132 and the biotissue is large. The time-power relation $P=f(\beta, t)$ for use in this case is, for example, a relation shown in FIG. 12B. That is, after the time tm, the power P to be supplied rises to the maximum power Pmax to be supplied, and this power is then maintained for a while. The time when the maximum power Pmax to be supplied is maintained is longer than that in the case where the contact area is moderate as shown in FIG. 11B, and this time is, for example, about seven to eight seconds. Afterward, the power gradually decreases. By this supply of the power, the temperature of the first high frequency electrode 132 is maintained at the desired temperature Top as shown in FIG. 12A.

It is to be noted that the time-power relations and the temperature changes shown in FIG. 10A, FIG. 10B, FIG. 11A, FIG. 11B, FIG. 12A and FIG. 12B are merely examples, and the present invention is not limited to these examples. The time-power relation may be set by precisely performing measurement in advance, or may be set on the basis of a result of analysis of heat transfer. Here, the three types of time-power relations have been described, but needless to say, more time-power relations may be set in advance, so that the time-power list may have more time-power relations.

As described above, according to the present embodiment, even when a relation between the resistance value and the temperature of the resistance patterns 143 is unknown or even when the temperature of the first high frequency electrode 132 or the second high frequency electrode 134 is unknown, the first high frequency electrode 132 or the second high frequency electrode 134 can be controlled to a suitable temperature. That is, even when the temperature of the resistance patterns is not known, irrespective of the contact area between the first high frequency electrode 132 or the second high frequency electrode 134 and the biotissue, the first high frequency electrode 132 or the second high frequency electrode 134 can be controlled to the suitable temperature, and the treatment can be performed at the desired temperature Top.

According to the present embodiment, it is not necessary to acquire the relation between the resistance value and the temperature of the resistance patterns 143, and hence a process of acquiring the relation between the resistance value and the temperature of the resistance patterns 143 can be cut. Moreover, by cutting out the process concerning the resistance pattern 143, costs of the energy treatment tool 120 can be decreased. Furthermore, according to the present embodiment, as compared with a case where the temperature of the heat generating chips 140 is acquired and feedback control is executed on the basis of the temperature, the structure of the device and the control of the device can be simplified.

It is to be noted that even when the power P0 to be supplied is supplied in a case where the contact area is 0 or an assumable minimum, it is preferable that at the point of time tm, the temperature of the first high frequency electrode 132 or the second high frequency electrode 134 is slightly lower than the desired temperature Top. When the power P0 is larger than such a power, there is the fear that the temperature of the first high frequency electrode 132 or the second high frequency electrode 134 is in excess of the desired temperature Top at the point of time tm, in the case where the contact area between the first high frequency electrode 132 or the second high frequency electrode 134 and the biotissue is small. On the other hand, when the power P0 is smaller than such a power, there is the fear that the temperature rise $\Delta T$ at the time tm is small and acquisition precision of the variable $\beta$ deteriorates, in the case where the contact area between the first high frequency electrode 132 or the second high frequency electrode 134 and the biotissue is large.

[First Modification]

In the above-mentioned embodiment, the type of energy treatment tool 120 is stored in the memory 123 of the energy treatment tool 120, and the time-power lists corresponding to the type of energy treatment tool 120 are stored in the storage section 187 of the controller 170. On the other hand, in the present modification, a time-power list corresponding to the energy treatment tool 120 is stored in the memory 123 of the energy treatment tool 120. In this time-power list, a relation between time and a power to be supplied is recorded for each variable β as shown in, for example, FIG. 13. In the memory 123 of each energy treatment tool 120, for example, such one time-power list is stored. Thus in the present modification, for example, the memory 123 functions as a storage section to store the time-power list.

In the present modification, the control section 180 reads the time-power list from the memory 123 in step S102. In step S209, a time-power relation corresponding to β calculated from the read time-power list is extracted. Also, according to the present modification, an operation is performed similarly to the above-mentioned embodiment, and similar effects can be obtained.

[Second Modification]

In the above-mentioned embodiment, at the time 0 to tm as the state detection period, the power P to be supplied=P0 is set, but this power is not limited to the predetermined value. The power may change with elapse of time. In this case, there may be specified a time-power relation for setting the temperature of the first high frequency electrode 132 or the second high frequency electrode 134 to the desired temperature Top on the basis of a value concerning the change of the resistance value during the supply of the power. For example, a predetermined power supplying pattern may be set beforehand, and a time-power relation corresponding to a variable β which can be obtained in the same manner as in the above-mentioned embodiment when the power is supplied in accordance with the power supplying pattern may be stored as a time-power list in the storage section 187. Furthermore, the state detection period may include a period when the power is not supplied.

Moreover, in the above-mentioned embodiment, the control section 180 acquires the resistance values of the resistance patterns 143 at the time 0 and the time tm, but the variable β may be calculated by using the resistance values of the resistance patterns 143 which are acquired at two other times for the time 0 to tm. Furthermore, in the above-mentioned embodiment, the ratio between the resistance value R0 of the resistance patterns 143 at the start of the power supply and the resistance value Rm thereof at the time tm is used as the variable β, but a value corresponding to the variable β is not limited to this example. The value may be, for example, an increase amount of the resistance value or an increase speed of the resistance value. When the time-power list has the value concerning the resistance value change calculated by any one of the above-mentioned methods, and the time-power relation in which the temperature of the first high frequency electrode 132 and the second high frequency electrode 134 corresponding to this value is the desired temperature Top, an operation is performed similarly to the above-mentioned embodiment, and similar effects can be obtained.

Furthermore, although not based on the resistance value, for example, the holding portion 125 may include a contact sensor which detects the contact area with the biotissue, and an output of this contact sensor may function similarly to the variable β. Furthermore, the first high frequency electrode 132 may include a temperature sensor, and an output of this temperature sensor may function similarly to the variable β.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
   a first treatment tool comprising:
      a heat transfer surface configured to transfer heat to a subject that is placed in thermal contact with the heat transfer surface; and
      a resistance element in thermal contact with the heat transfer surface, wherein the resistance element is configured to be powered to generate heat that is transferred to the heat transfer surface to heat the subject; and
   a resistance value acquiring circuit configured to acquire a resistance value R0 of the resistance element at a first time and a resistance value Rm of the resistance element at a second time subsequent to the first time, the first time and the second time defining a state detection period;
   a power source configured to power the resistance element; and
   a controller configured to:
      calculate a voltage of value V0 to be applied to the resistance element in the state detection period, the voltage of value V0 being calculated based on the resistance value R0 and a predetermined power P0 to be supplied to the resistance element in the state detection period;
      control the power source over the state detection period to apply the voltage of value V0 to the resistance element;
      calculate a change of the resistance value in the state detection period based on the resistance value R0 and the resistance value Rm;
      determine a time-power relation based on the change of the resistance value, wherein the time-power relation defines a power supplied by the power source to the resistance element over a control time period after the state detection period to heat the first treatment tool to a desired temperature;
      calculate values of voltage to be applied to the resistance element over the control time period based on the time-power relation; and
      control the power source over the control time period to apply the voltage at the values calculated to the resistance element to heat the first treatment tool to the desired temperature.

2. The treatment device according to claim 1, wherein a maximum value of the predetermined power P0 is smaller than a maximum value of the power defined by the time-power relation.

3. The treatment device according to claim 1, wherein the controller is further configured to:
   calculate, as the change of the resistance value in the state detection period, a ratio between the resistance value R0 and the resistance value Rm, and
   determine the time-power relation based on the ratio.

4. The treatment device according to claim 1, wherein the predetermined power P0 has a constant value.

5. The treatment device according to claim 1, wherein the controller is configured to be detachably connectable to the first treatment tool,
wherein the first treatment tool has type identification information which specifies the first treatment tool as being a treatment tool of a first type,
wherein the treatment device further comprises a memory configured to store at least:
   a first time-power relation corresponding to the treatment tool of the first type; and a second time-power relation corresponding to a treatment tool of a second type different from the first type, and wherein the controller is configured to acquire from the memory, when the controller is connected to the first treatment tool, the first time-power relation based on the type identification information.

6. The treatment device according to claim 1,
wherein the controller is configured to be detachably connected to the first treatment tool and to be detachably connected to a second treatment tool,
wherein the first treatment tool comprises a first memory configured to store a first time-power relation as the time-power relation,
wherein the second treatment tool comprises a second memory configured to store a second time-power relation as the time-power relation,
wherein the controller is configured to acquire, when the controller is connected to the first treatment tool, the first time-power relation from the first memory, and
wherein the controller is configured to acquire, when the controller is connected to the second treatment tool, the second time-power relation from the second memory.

7. The treatment device according to claim 2,
wherein the controller is further configured to:
calculate, as the change of the resistance value in the state detection period, a ratio between the resistance value R0 and the resistance value Rm, and
determine the time-power relation based on the ratio.

8. The treatment device according to claim 2,
wherein the predetermined power P0 has a constant value.

9. The treatment device according to claim 2,
wherein the controller is configured to be detachably connected to the first treatment tool,
wherein the first treatment tool has type identification information which specifies the first treatment tool as being a treatment tool of a first type,
wherein the treatment device further comprises a memory configured to store at least:
  a first time-power relation as the time-power relation, wherein the first time-power relation corresponds to the treatment tool of the first type; and
  a second time-power relation as the time-power relation, wherein the second time-power relation corresponds to a treatment tool of a second type different from the first type, and
wherein the controller is configured to acquire from the memory, when the controller is connected to the first treatment tool, the first time-power relation based on the type identification information.

10. The treatment device according to claim 2,
wherein the controller is configured to be detachably connected to the first treatment tool and to be detachably connected to a second treatment tool,
wherein the first treatment tool comprises a first memory configured to store a first time-power relation as the time-power relation,
wherein the second treatment tool comprises a second memory configured to store a second time-power relation as the time-power relation,
wherein the controller is configured to acquire, when the controller is connected to the first treatment tool, the first time-power relation from the first memory, and
wherein the controller is configured to acquire, when the controller is connected to the second treatment tool, the second time-power relation from the second memory.

11. A controller device for controlling a treatment device, wherein the treatment device comprises:
a first treatment tool comprising:
  a heat transfer surface configured to transfer heat to a subject that is placed in thermal contact with the heat transfer surface; and
  a resistance element in thermal contact with the heat transfer surface, wherein the resistance element is configured to be powered to generate heat that is transferred to the heat transfer surface to heat the subject;
a resistance value acquiring circuit configured to acquire a resistance value R0 of the resistance element at a first time and a resistance value Rm of the resistance element at a second time subsequent to the first time, the first time and the second time defining a state detection period; and
a power source configured to power the resistance element, and
wherein the controller device comprises:
a controller configured to:
  calculate a voltage of value V0 to be applied to the resistance element in the state detection period, the voltage of value V0 being calculated based on the resistance value R0 and a predetermined power P0 to be supplied to the resistance element in the state detection period;
  control the power source over the state detection period to apply the voltage of value V0 to the resistance element;
  calculate a change of the resistance value in the state detection period based on the resistance value R0 and the resistance value Rm;
  determine a time-power relation based on the change of the resistance value, wherein the time-power relation defines a power supplied by the power source to the resistance element over a control time period after the state detection period to heat the first treatment tool to a desired temperature;
  calculate values of voltage to be applied to the resistance element over the control time period based on the time-power relation; and
  control the power source over the control time period to apply the voltage at the values calculated to the resistance element to heat the first treatment tool to the desired temperature.

12. The controller device according to claim 11,
wherein a maximum value of the predetermined power P0 is smaller than a maximum value of the power defined by the time-power relation.

13. The controller device according to claim 11,
wherein the controller is further configured to:
calculate, as the change of the resistance value in the state detection period, a ratio between the resistance value R0 and the resistance value Rm, and
determine the time-power relation based on the ratio.

14. The controller device according to claim 11,
wherein the predetermined power P0 has a constant value.

15. The controller device according to claim 11,
wherein the controller is configured to be detachably connectable to the first treatment tool,
wherein the first treatment tool has type identification information which specifies the first treatment tool as being a treatment tool of a first type,
wherein the controller device further comprises a memory configured to store at least:
  a first time-power relation corresponding to the treatment tool of the first type; and a second time-power relation corresponding to a treatment tool of a second type different from the first type, and wherein the controller is configured to acquire from the memory, when the controller is connected to the first treatment tool, the first time-power relation based on the type identification information.

16. The controller device according to claim 11, wherein the controller is configured to be detachably connected to the first treatment tool and to be detachably connected to a second treatment tool, wherein the first treatment tool comprises a first memory configured to store a first time-power relation as the time-power relation, wherein the second treatment tool comprises a second memory configured to store a second time-power relation as the time-power relation, wherein the controller is configured to acquire, when the controller is connected to the first treatment tool, the first time-power relation from the first memory, and wherein the controller is configured to acquire, when the controller is connected to the second treatment tool, the second time-power relation from the second memory.

17. The controller device according to claim 12, wherein the controller is further configured to:
calculate, as the change of the resistance value in the state detection period, a ratio between the resistance value R0 and the resistance value Rm, and
determine the time-power relation based on the ratio.

18. The controller device according to claim 12, wherein the predetermined power P0 has a constant value.

19. The controller device according to claim 12, wherein the controller is configured to be detachably connected to the first treatment tool, wherein the first treatment tool has type identification information which specifies the first treatment tool as being a treatment tool of a first type, wherein the controller device further comprises a memory configured to store at least:
a first time-power relation as the time-power relation, wherein the first time-power relation corresponds to the treatment tool of the first type; and
a second time-power relation as the time-power relation, wherein the second time-power relation corresponds to a treatment tool of a second type different from the first type, and wherein the controller is configured to acquire from the memory, when the controller is connected to the first treatment tool, the first time-power relation based on the type identification information.

20. The controller device according to claim 12, wherein the controller is configured to be detachably connected to the first treatment tool and to be detachably connected to a second treatment tool, wherein the first treatment tool comprises a first memory configured to store a first time-power relation as the time-power relation, wherein the second treatment tool comprises a second memory configured to store a second time-power relation as the time-power relation, wherein the controller is configured to acquire, when the controller is connected to the first treatment tool, the first time-power relation from the first memory, and wherein the controller is configured to acquire, when the controller is connected to the second treatment tool, the second time-power relation from the second memory.

* * * * *